United States Patent
Moulin et al.

(10) Patent No.: US 10,076,289 B2
(45) Date of Patent: Sep. 18, 2018

(54) EXAMINATION TABLE OF MEDICAL IMAGING SYSTEM

(71) Applicant: GENERAL ELECTRIC COMPANY, Schenectady, NY (US)

(72) Inventors: Romain Moulin, Paris (FR); Bruno Galloni, Saint Lubin des Joncherets (FR)

(73) Assignee: General Electric Company, Schenectady, NY (US)

( * ) Notice: Subject to any disclaimer, the term of this patent is extended or adjusted under 35 U.S.C. 154(b) by 151 days.

(21) Appl. No.: 15/180,035

(22) Filed: Jun. 12, 2016

(65) Prior Publication Data

US 2017/0020466 A1 Jan. 26, 2017

Related U.S. Application Data

(63) Continuation of application No. PCT/IB2013/002947, filed on Dec. 12, 2013.

(51) Int. Cl.
| | | |
|---|---|---|
| *A61G 13/02* | (2006.01) | |
| *A61B 6/04* | (2006.01) | |
| *A61G 13/00* | (2006.01) | |
| *A61G 13/12* | (2006.01) | |

(52) U.S. Cl.
CPC .......... *A61B 6/0442* (2013.01); *A61B 6/0457* (2013.01); *A61G 13/0018* (2013.01); *A61G 13/02* (2013.01); *A61G 13/126* (2013.01)

(58) Field of Classification Search
CPC ................................ A61G 13/02; A61G 13/04

USPC ..................................... 5/601, 600, 81.1 HS
See application file for complete search history.

(56) References Cited

U.S. PATENT DOCUMENTS

| | | | | |
|---|---|---|---|---|
| 4,700,938 A | * | 10/1987 | Chambron ........... | A61B 6/0457 378/209 |
| 6,769,145 B1 | * | 8/2004 | Pfeuffer ............... | A61B 6/0442 378/209 |
| 2004/0255383 A1 | * | 12/2004 | Longton .................. | A61B 6/04 5/601 |
| 2012/0049084 A1 | | 3/2012 | Abenaim et al. | |

FOREIGN PATENT DOCUMENTS

DE       102004013585 A1    10/2005

OTHER PUBLICATIONS

International Search Report and Written Opinion for PCT/IB2013/002947, dated Jul. 8, 2014, 10 pages.

* cited by examiner

*Primary Examiner* — Fredrick C Conley
(74) *Attorney, Agent, or Firm* — GE Global Patent Operation; Marc A. Vivenzio

(57) ABSTRACT

This disclosure relates to an examination table of a medical imaging system comprising a tabletop, a table column supporting the tabletop, and a translation system. The translation system, which is configured to at least make the tabletop longitudinally translate with respect to the table column, comprises a guiding part and a driving part, where both the guiding and driving parts may be fully integrated in said table column.

8 Claims, 2 Drawing Sheets

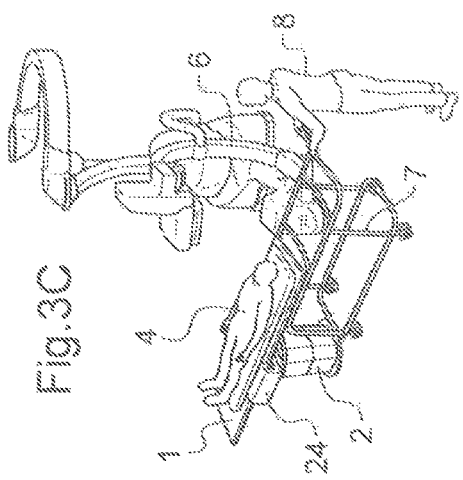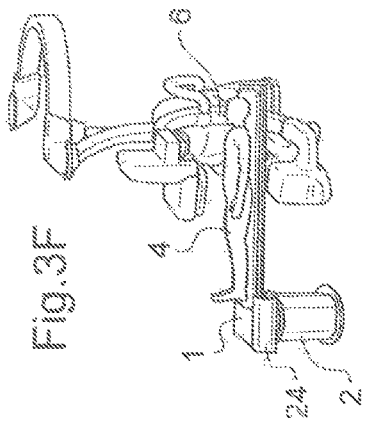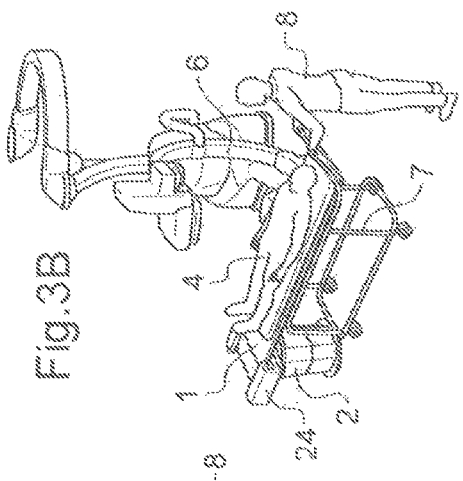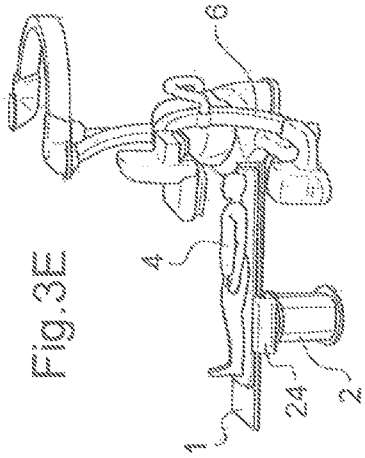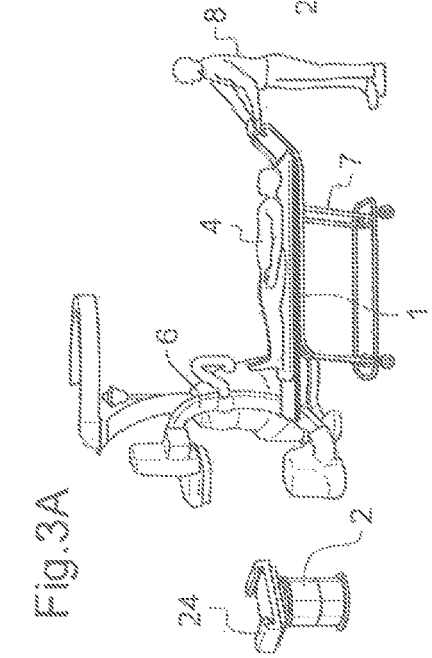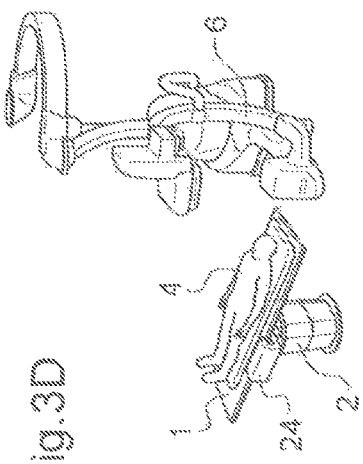

EXAMINATION TABLE OF MEDICAL IMAGING SYSTEM

CROSS-REFERENCE TO RELATED APPLICATIONS

This application is a continuation of co-pending International (PCT) Application No. PCT/IB2013/002947, filed Dec. 12, 2013, the contents of which are incorporated by reference herein.

TECHNICAL FIELD

The exemplary non-limiting embodiment described herein relate to examination tables of medical imaging system and associated tabletops of said examination tables.

BACKGROUND

According to a first prior art, for example described in the patent application US 2008/0045831, it is known an examination table including a longitudinal translation system, allowing for a tabletop transfer from and to a table support. However, the tabletop includes part of the longitudinal translation system and more particularly part of the guiding part of the translation system, which makes transfer not that easy or simple. Besides, this longitudinal translation system deals with the transfer of the tabletop from and to the table support, not with the longitudinal translation of the tabletop with respect to the table support while the tabletop remains on the table support.

According to a second prior art, for example described in a brochure on the web "Maquet awigs table", at the Internet address [http://www.maquet.com/content/SurgicalWorkplaces/Documents/Brochures/IGS_MSW_BR_10000008_EN_2_NONUS_V.pdf], it is known an examination table including a longitudinal translation system, allowing for a tabletop transfer from and to a table support. However, the tabletop includes part of the longitudinal translation system and more particularly some rails of the guiding part of the translation system, what makes transfer not that easy or simple. Besides, this longitudinal translation system deals with the transfer of the tabletop from and to the table support, not with the longitudinal translation of the tabletop with respect to the table support while the tabletop remains on the table support.

SUMMARY

The exemplary non-limiting embodiments described herein to alleviate the above mentioned drawbacks.

More particularly, the exemplary non-limiting embodiments described herein aim to provide an examination table including a tabletop moving or sliding on a table support being usually a table column, which examination table allows for an easier and simpler transfer of the tabletop from and to the table support, while on at the same time providing for a shorter length of tabletop for a wished stroke of longitudinal translation which is usually rather long.

The exemplary non-limiting embodiments described herein further aim to provide a table support including the guiding part as well as driving part of the longitudinal translation system of the tabletop with respect to the table support while the tabletop remains on the table support. That way, the tabletop including neither the guiding part nor the driving part of this longitudinal translation system, not only is the tabletop exchange made easier, because there are no or less protruding elements on the tabletop, but also the length of the tabletop, for a given and usually rather long stroke of longitudinal translation, is shortened, because no guiding element extends over an extremity of the tabletop.

The exemplary non-limiting embodiments of the tabletop described herein includes neither the guiding part nor the driving part of this longitudinal translation system, also takes benefit of a second and unexpected effect, which is the high transparency of most of, if not of all, the tabletop to the X-ray, allowing for better and simpler imaging of the patient when the tabletop is longitudinally shifted with respect to the table support, so that the tabletop becomes then alone within the field of the imaging device of the medical imaging system, thereby causing little or no artifact in the images taken by this imaging device, especially and preferably when the imaging device is an X-ray imaging device.

Indeed, the guiding and driving parts of the longitudinal translation system present protuberances that would interfere and lessen the image quality thereby disturbing the corresponding diagnostic, all the more if those guiding and driving parts, comprising for example rails, include metallic parts.

This advantage is achieved with an examination table of medical imaging system, comprising a tabletop, a table column supporting said tabletop, a translation system which is configured to make said tabletop longitudinally translate with respect to said table column and which comprises a guiding part and a driving part, wherein both said guiding and driving parts are fully integrated in said table column.

This advantage is also achieved with a tabletop of an examination table of medical imaging system, wherein it comprises no portion either of the guiding part or of the driving part of a translation system of said examination table which is configured to make said tabletop longitudinally translate with respect to a table column of said examination table supporting said tabletop.

This advantage is also achieved with a translation method, making a tabletop of an examination table of medical imaging system longitudinally translate with respect to a table column of said examination table supporting said tabletop, by using guiding and driving parts of a translation system which are both fully integrated in said table column.

This advantage is also achieved with a patient installation method from outside an examination table and on said examination table which includes a table column configured to support a tabletop and a translation system which is configured to make a tabletop longitudinally translate with respect to said table column and which comprises a guiding part and a driving part, both said guiding and driving parts being fully integrated in said table column, said patient installation method comprising a longitudinal translation step of a tabletop supporting a patient from outside said table column on said table column, said longitudinal translation step including only horizontal move(s) without any vertical move. Preferably, this longitudinal translation step of the tabletop is the only step of the patient installation method.

Exemplary non-limiting embodiments comprise one or more of the following features, which can be taken separately or together, either in partial combination or in full combination; these features can also be taken in combination with any of the preceding aspects.

In at least one exemplary non-limiting embodiment, said guiding part is configured to cooperate directly with at least a lateral edge of said tabletop. That way, only the shape of the edge(s) of the tabletop needs to present a specific shape different from flat. This means that images may be disturbed by specific shape only when such images are taken with inclined radiation corresponding to the lateral extremities of the tabletop, what happens relatively seldom, at least not so often than images of the center portion of the tabletop.

In at least one exemplary non-limiting embodiment, said guiding part is configured to cooperate only with one or more lateral edges of said tabletop. That way, the tabletop presents practically no more protruding part.

In at least one exemplary non-limiting embodiment, said driving part is configured to cooperate either only with one or more lateral edges of said tabletop or only with tabletop flat zones neighboring lateral edges of said tabletop. Similar advantages can be derived as the advantages from the guiding part cooperating with one or more lateral edges of said tabletop.

In at least one exemplary non-limiting embodiment, said driving and guiding parts share common rollers, said common rollers being preferably at least two, said common rollers being more preferably at least four. That way, the structure of the global longitudinal translation system is made simpler because it contains fewer elements.

In at least one exemplary non-limiting embodiment, said guiding part comprises said common rollers and lateral rails fully integrated in said table column, said common rollers being disposed within said lateral rails. This structure is robust and efficient.

In at least one exemplary non-limiting embodiment, said driving part comprises said common rollers and a motorization fully integrated in said table column, said motorization driving rotation of said common rollers.

In at least one exemplary non-limiting embodiment, said common rollers cooperate with one or more said tabletop lateral edges by direct friction between each other. That way, the structure of the global longitudinal translation system is quite simple, since motion is directly transmitted from motorization to tabletop itself via only a single stage which is the roller(s). There is a direct friction between tabletop lateral edges and corresponding rollers.

In at least one exemplary non-limiting embodiment, all of the common rollers present a vertical rotation axis. This is then easier for these common rollers to drive the tabletop in a longitudinal translation, because these common rollers sandwich the entire width of the tabletop.

In at least one exemplary non-limiting embodiment, said tabletop lateral edges present a convex shape, preferably a narrowing out shape, more preferably a triangular shape. This raises and improves the direct friction of the tabletop lateral edges against the rollers. To further improve this direct friction, springs or other elastic elements may be associated to the rollers and may be disposed so as to push all or part of the rollers against the lateral edges of the tabletop.

In at least one exemplary non-limiting embodiment, said tabletop comprises inner foam surrounded by an outer casing comprising no other protruding part than its edges, said outer casing including preferably one or more carbon fiber sheets, and said tabletop lateral edges presenting an outer casing which is preferably reinforced as compared to the rest of said tabletop. This makes tabletop structure simple, robust, light and highly transparent to X-ray radiation, all features being especially interesting when the tabletop is longitudinally shifted with respect to the table column so as to come into the field of the imaging device.

In at least one exemplary non-limiting embodiment, said tabletop includes barcodes which are printed on its external surface and which are representative of values of translation distances of said tabletop with respect to said table column. These barcodes comprise useful information to control the amplitude of the longitudinal translation of the tabletop with respect to the table column, while simultaneously presenting no notable protrusion from tabletop and being highly transparent to X-ray radiation.

In at least one exemplary non-limiting embodiment, one or more lateral edges of said tabletop are configured to cooperate directly with said guiding part of said examination table.

In at least one exemplary non-limiting embodiment, said tabletop presents a length of at least 1500 mm without any metallic part, more preferably a length of at least 1700 mm without any metallic part, what improves global transparency to X-ray of the tabletop.

In at least one exemplary non-limiting embodiment, said table column preferably presents a length of at most 800 mm, more preferably a length of at most 600 mm, what reduces total bulk of the table column.

In at least one exemplary non-limiting embodiment, said examination table presents 6 freedom degrees, among which 3 translation degrees and 3 rotation degrees, the tabletop presenting, with respect to the table column, only a longitudinal translation degree.

In at least one exemplary non-limiting embodiment, said medical imaging system includes a C-arm or a computed tomography.

In at least one exemplary non-limiting embodiment, said medical imaging system includes a floor gantry or is fixed to the ceiling or is supporting on a vehicle.

In at least one exemplary non-limiting embodiment, at least one of the longitudinal edges of tabletop presents a convex shape.

In at least one exemplary non-limiting embodiment, said medical imaging system uses X-ray radiation for imaging.

In at least one exemplary non-limiting embodiment, said tabletop is integral and/or comprises a single tray, except for a mattress which can be fixed on it or supported by it.

In at least one exemplary non-limiting embodiment, said tabletop is completely passive and/or does not include any metallic part.

In at least one exemplary non-limiting embodiment, said horizontal move consists only in a rectilinear translation.

Further features and advantages of the exemplary non-limiting embodiments described herein will appear from the following description of exemplary non-limiting embodiments described herein, with reference to the accompanying drawings listed hereunder.

BRIEF DESCRIPTION OF THE DRAWINGS

FIGS. 3A to 3F show different steps of an example of a patient installation method according to the exemplary non-limiting embodiments described herein.

DETAILED DESCRIPTION

Figure 1:
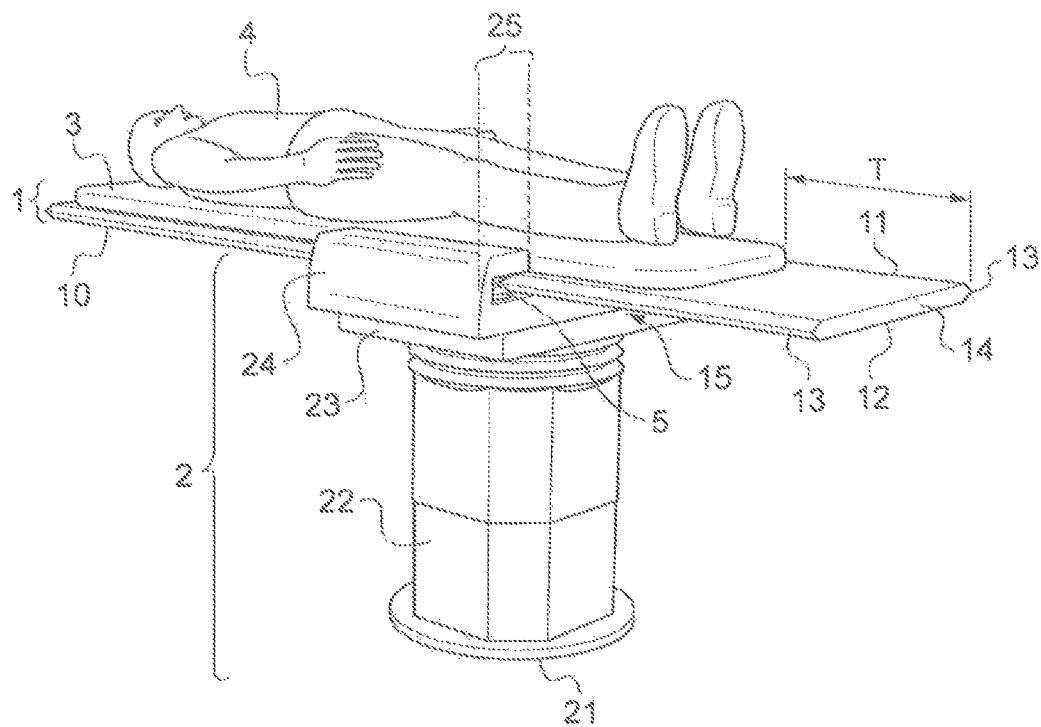
FIG. 1 shows a perspective view of an example of an examination table according to the exemplary non-limiting embodiments described herein.

FIG. 1 shows a perspective view of an example of an examination table according to an exemplary non-limiting embodiment. The examination table comprises a tabletop 1 supported by a table column 2. On the tabletop 1 lies a patient 4. The tabletop 1 comprises a tray 10 on which is disposed or fixed a mattress 3 on which in turn the patient 4 directly lies. The mattress 3 is softer than the tray 10, for patient's 4 improved comfort and stability.

The tray 10 of the tabletop 1 comprises a flat upper face 11 and a flat lower face 12. These flat upper face 11 and flat lower face 12 are bound together by edges, lateral edges 13 and longitudinal edges 14. Lateral edges 13 and longitudinal edges 14 present a narrowing out shape, preferably a triangular shape with the spike pointing outward.

Barcodes 15, representative of longitudinal positions, may be printed under the lower face 12 of the tray 10. By reading these printed barcodes 15, the driving part of the table column 2 detects the tabletop 1 position and may stop the longitudinal translation of the tabletop 1 at will.

The table column 2 comprises a pivoting part 21, a central part 22, an intermediate part 23 and a guiding part 24. The pivoting part 21 is configured to make the central part 22 pivoting around a vertical axis. When the central part 22 is pivoting, the intermediate part 23, the guiding part, and the tabletop 1, are pivoting too.

The central part 22 is configured to make the intermediate part 23 lifting, tilting and/or cradling. When the intermediate part 23 is respectively lifting, tilting or cradling, the guiding part and the tabletop 1 are respectively lifting, tilting or cradling too.

The intermediate part 23 is configured to perform a lateral translation on rails of the guiding part 24. When the guiding part 24 is making a lateral translation, the tabletop 1 is making a lateral translation too. Lateral translation stroke can be plus or minus 300 mm for example.

The guiding part 24 comprises rollers 5 disposed within lateral rails 25 in form of a quarter turn rotated U. The guiding part 24 is configured to perform a longitudinal translation of the tabletop 1, the tabletop 1 sliding by direct friction of its lateral edges 13 on the rollers 5 so as to longitudinally translate with respect to the guiding part 24 and with respect to the whole table column 2. A double arrow T represents the direction of the longitudinal translation which can be performed from forward to backward and from backward to forward, forward being on the side of the patient 4 head and backward being on the side of the patient 4 feet. The longitudinal translation stroke of the tabletop 1 is sufficient for all the part of the tray 10 of the tabletop 1 supporting the mattress 3 to be shifted so as to no more overhang the guiding part 24 of the table column 2, while the remaining part of the tray 10 being still guided by the guiding part 24 is sufficiently long so as to support and keep the whole tabletop 1 in place and horizontal. The part of the tray 10 of the tabletop 1 supporting the mattress 3 which is also the part of the tray 10 of the tabletop 1 that can be shifted so as to no more overhang the guiding part 24 of the table column 2, is preferably at least 1700 mm long.

Figure 2:
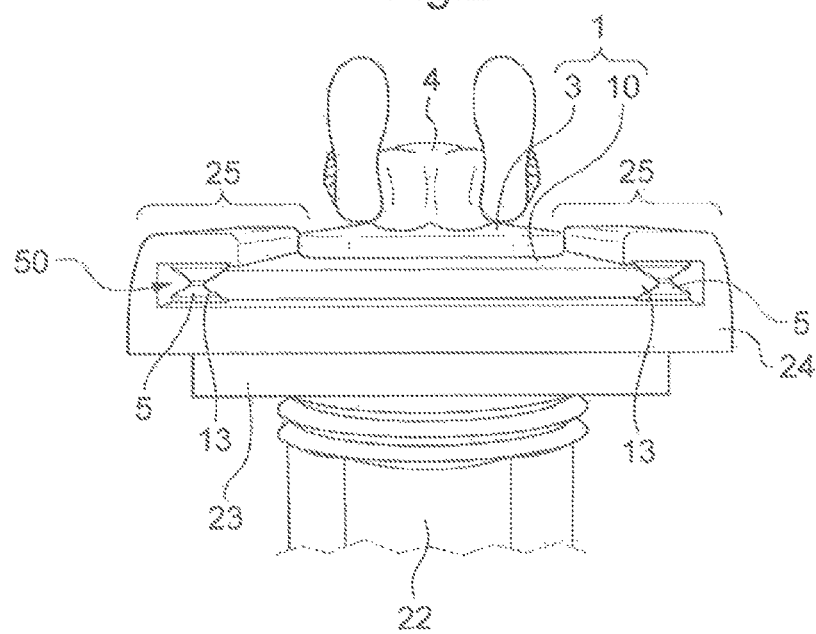
FIG. 2 shows a rear view of an example of an examination table according to the exemplary non-limiting embodiments described herein.

FIG. 2 shows a rear view of an example of an examination table according to an exemplary non-limiting embodiment. This rear view appears to be slightly in perspective too. The lateral edges 13 of the tabletop 1 present a triangular shape which spike is outwards towards the V shaped recess of the rollers 5. The rollers 5 each present a shape corresponding to two cones joined by their top so as to present a V shaped recess configured to cooperate with the spike of the triangular shape of the lateral edges 13.

There are two rollers 5 on each side of the tabletop 1. Springs 50 are pushing the rollers 5 against the lateral edges 13 of the tabletop 1 so as to guarantee a sufficient level of direct friction between these rollers 5 and the corresponding lateral edges 13 of the tabletop 1. Springs 50 may be on one lateral side of the tabletop 1 only, or on both lateral sides of the tabletop 1. These rollers 5 serve as guiding devices of the tabletop 1. These rollers 5 also serve here as driving devices causing the longitudinal translation of the tabletop 1. Therefore, these rollers 5 are motorized, which means there is a motor in the table column 2 which causes the rotation, around a vertical axis, of the rollers 5 which in turn drive the longitudinal translation of the tabletop 1. Those rollers 5 are friction rollers 5.

As an alternative, not represented on FIG. 2, the rollers 5 may only serve as guiding devices, other rollers rotating around horizontal axis and being disposed under the tray 10 so as to drive by friction the tray 10 during its longitudinal translation.

When considering a section of the tray 10 of the tabletop 1, the tray 10 presents an inner foam surrounded by an outer casing made of one or more carbon fiber sheets or layers, preferably 2 carbon fiber sheets or layers. The lateral edges 13 are reinforced as compared to the rest of the tray 10. For example, the lateral edges 13 of the tray 10 may comprise 3 or 4 carbon fiber sheets or layers.

FIGS. 3A to 3F show different steps of an example of a patient installation method according to an exemplary non-limiting embodiment.

In FIG. 3A, there are a C-arm 6 on a vehicle, a cart 7, a nurse 8, as well as the tabletop 1, the table column 2 surmounted by its guiding part 24, and the patient 4. The patient 4 is lying on the tabletop 1 which is supported by a cart 7 pushed by the nurse 8. The nurse 8 is bringing the patient 4, for example from his or her room, into the examination room where the C-arm 6 and the table column 2 are stationary, to perform imaging of a portion of his or her body.

In FIG. 3B, the nurse 8 brings the cart 7 close to the table column 2, so as to be able to transfer the tabletop 1 and the patient 4 supported by the tabletop 1 from the cart 7 on the table column 2. Without any vertical lift of the tabletop 1 and without need to remove the patient 4 from the tabletop 1, the tabletop 1 starts sliding horizontally from the cart 7 onto the table column 2, so as to insert the tabletop 1 into the guiding part 24 of the table column 2.

In FIG. 3C, the longitudinal translation of the tabletop 1 in the guiding part 24 of the table column 2 is performed along the guiding part 24. The cart 7 is removed by the nurse 8 from the vicinity of the table column 2 so that the tabletop 1 is no more supported by the cart 7 but by the table column 2.

In FIG. 3D, the nurse 8 pushes the cart 7 out of the examination room, so as to leave the patient 4 and its supporting tabletop 1 on the table column 2.

In FIG. 3E, the table column 2 pivots so that the tabletop 1 pivots too in order to be oriented along the axis of the C-arm 6.

In FIG. 3F, the table column 2 performs the longitudinal translation of the tabletop 1 forward, so that the tabletop 1 and its supported patient 4 come within the C-arm 6. Then, the X-ray imaging device of the C-arm 6 can make the shots of the region of interest of the body of the patient 4. Between two shots or between two series of shots, a longitudinal translation may be continued so that another portion of the body of the patient 4 becomes within the field of the X-ray imaging device. The imaging device preferably uses an X-ray source and detector, but could alternatively use a source and a detector which are sensitive to another part of the radiation spectrum.

Instead of a C-arm 6 on vehicle, the imaging device could be a computed tomography for example or another imaging device.

While the invention has been described in detail in connection with a limited number of exemplary non-limiting embodiments, it should be readily understood that the invention is not limited to such disclosed embodiments. Rather, the above embodiments can be modified to incorporate any number of variations, alterations, substitutions or equivalent arrangements not heretofore described, but which are commensurate with the spirit and scope of the invention. Additionally, while various embodiments have been described, it is to be understood that aspects of the invention may include any or all of the described features of said embodiments. Accordingly, the invention is not to be seen as limited by the foregoing description, but is only limited by the scope of the appended claims.

What is claimed is:

1. An examination table for a medical imaging system, comprising:
    a tabletop defining a patient support surface and opposing lateral edges;
    a table column supporting said tabletop; and
    a translation system forming part of the column and configured to effectuate a longitudinal translation of said tabletop with respect to said table column, said translation system comprising a pair of guide rails laterally spaced relative to the tabletop, each of the pair of guide rails defining a respective groove through which the tabletop translates, and two sets of motorized rollers, each set comprising two opposing rollers rotatable about a vertical axis relative to the patient support surface and configured to cooperate directly with the opposing lateral edges of said tabletop.

2. The examination table according to claim 1, wherein said tabletop includes barcodes which are printed on its external surface, each of which are representative of a respective longitudinal position of the tabletop relative to with respect to said table column, the translation system configured to detect the barcodes and to stop longitudinal translation of the tabletop at any of the longitudinal positions associated with their respective barcode.

3. The examination table according to claim 1, wherein said translation system is configured to cooperate exclusively with the opposing lateral edges of said tabletop.

4. The examination table according to claim 1, wherein the opposing rollers in each set are conical shaped and positioned so their respective vertexes face each other so as to define a respective v-shaped recess configured to cooperate with a respective one of the opposing lateral edges of said table top.

5. The examination table according to claim 4, wherein the two sets of motorized rollers cooperate with said tabletop lateral edges by direct friction between each other.

6. The examination table according to claim 4, wherein each of said tabletop lateral edges defines a triangular convex shape configured to fit into and cooperate with a corresponding one of the v-shaped recess formed by the opposing rollers in each of the two sets of motorized rollers.

7. The examination table according to claim 1, wherein said translation system comprises a motor fully integrated in said table column, said motor configured to drive rotation of the two sets of motorized rollers.

8. The examination table according to claim 1, wherein said tabletop comprises an inner foam surrounded by an outer casing comprising no other protruding part other than its defining edges, said outer casing including one or more carbon fiber sheets, and said tabletop lateral edges present an outer casing which is structurally more rigid relative to the rest of said tabletop.

* * * * *